United States Patent
Kramer et al.

[11] Patent Number: 5,938,636
[45] Date of Patent: Aug. 17, 1999

[54] AUTOINFUSER FOR RESUSCITATION AND METHOD OF INFUSION FLUID INJECTION

[75] Inventors: George C. Kramer, Galveston, Tex.; Jerald M. Henderson, Chico, Calif.; Wendy R. Feenstra, Bedford, Mass.; Domenico Castaldo, Galveston, Tex.

[73] Assignees: The Bd of Regents of the University of California, Oakland, Calif.; The Bd of Regents of the University of Texas, Austin, Tex.

[21] Appl. No.: 08/880,005

[22] Filed: Jun. 20, 1997

[51] Int. Cl.[6] .................................................. A61M 31/00

[52] U.S. Cl. ............................. 604/66; 604/67; 604/141

[58] Field of Search ............................. 604/65–67, 131, 604/140, 141

[56] References Cited

U.S. PATENT DOCUMENTS 4,568,330  2/1986  Kujawski et al. ........................ 604/53

*Primary Examiner*—Corrine McDermott
*Attorney, Agent, or Firm*—Rosenblatt & Redano P.C.

[57] ABSTRACT

The present invention relates to an apparatus for injecting infusion fluids into a patient at a controlled infusion rate. This apparatus is referred to as a "controlled autoinfuser". A preferred embodiment of the invention comprises a computer capable of using pressure volume and relationships to generate a control signal that will control the injection of infusion fluids into a patient. The present invention further comprises a method of controlling the injection of infusion fluids into a patient through the use of a microprocessor controlled autoinfuser as well as a method of injecting a preselected volume of infusion fluid into a patient within a preselected infusion time.

13 Claims, 8 Drawing Sheets

AUTOINFUSER FOR RESUSCITATION AND METHOD OF INFUSION FLUID INJECTION

This invention was made with Government support under Grant No. HL40296, awarded by the National Institutes of Health. The Government has certain rights in this invention.

BACKGROUND OF THE INVENTION

1. Field of the Invention

The present invention relates to an apparatus for injecting infusion fluids into a patent at a controlled infusion rate. This apparatus is referred to as a "controlled autoinfuser" A preferred embodiment of the invention comprises a computer capable of using the pressure volume relationships as defined by gas laws to generate a control signal that will control the injection of infusion fluids into a patient. In another embodiment, the present invention comprises a method of controlling the injection of infusion fluids into a patient through the use of a microprocessor controlled autoinfuser as well as a method of injecting a preselected volume of infusion fluid into a patient within a preselected infusion time without the use of a microprocessor.

2. Description of the Prior Art

Trauma is a leading cause of death in America. The optimal treatment of trauma is to stop bleeding and infuse saline solutions into the traumatized victim in order to restore blood volume, cardiac output, and pressure. Saline solutions are normally infused into peripheral vein catheters, but can also be delivered into the circulation by infusing directly into bone marrow using an intraosseous needle or intraosseous vascular access device.

Prior art infusion methods comprise the infusion of fluids to normalize cardiovascular function. One drawback of this method is that rapid increases in blood pressure can reopen clotted injuries and can increase internal bleeding and thereby actually increase mortality. As a result of this danger, some hospitals or trauma centers have policies of no prehospital resuscitation administration of fluid. This prior art method may prevent an increase in internal blood loss in many patients; however, it does not improve blood pressure and flow to those patients with cardiovascular functions below immediately life threatening critical levels.

Although it may be possible for a paramedic to monitor blood pressure or another physiological variable in order to infuse fluids as needed to reach and maintain a level of cardiovascular function necessary to sustain vital functions, such a practice requires extreme diligence on the part of the paramedic and limits or precludes the paramedic from attending to other important tasks. The present invention overcomes the weaknesses of the prior art by providing an automated means of prehospital resuscitation which does not rapidly increase blood pressure or needlessly increase internal bleeding while resuscitating the victim to a level of cardiovascular performance that maintains vital organ functions.

A variety of devices exist for infusing fluids into a body. One of such devices is a programmable infusion system, as disclosed in U.S. Pat. No. 5,078,683 to Sancoff et al. This patent discloses the use of a peristaltic pump comprising nine individual fingers which slide back and forth along a tubing segment which contains infusion fluid. Autoinfusers comprising such moving parts are complex and expensive.

Other prior art devices for the delivery of infusion fluids comprise syringe pumps. Such devices utilize a syringe wherein a piston travels through an outer cylinder containing infusion fluid in order to push the fluid Into a patient. The bottom portion of the piston comprises one or more seals to prevent infusion fluids from leaking out around the outer radial portion of the piston. Such pumps are useful for drug delivery in small volumes, but syringe size limits these pumps to volumes less than needed for resuscitation of shock. Prior art controlled infusion devices have many moving parts and require energy sources to move those parts and pump fluid.

Another limitation of current infusion pumps is that they are designed for low pressure infusion (300 mm Hg or less) needed for intravenous fluid delivery. Such pumps would be inefficient for the high pressure fluid delivery required of intraosseous fluid delivery. There is a need for a simple, less expensive controlled infusion system that can be used for intraosseous and intravenous fluid delivery in the prehospital and field environments. The size, weight, and complexity of prior art infusion devices is another drawback, particularly in field settings, as opposed to hospital settings.

Another embodiment is a method which uses the pressure volume relationship to set the initial volume, pressure and outflow resistance of a pressurized fluid container in order to deliver a total fluid volume with a predetermined flow rate or in a predetermined time interval.

SUMMARY OF THE INVENTION

The invention comprises a pressurized infuser comprising a fluid volume pressure container having a pressurized fluid occupying a known initial volume, $V_i$, and a known initial pressure, $P_i$. The pressurized fluid may be a gas. The pressurized infuser further comprises a flexible infusion fluid bag having volume $V_f$ contained within the pressure container, and an infusion fluid outlet port in fluid communication with the bag such that $V_i+V_f=V_c$. The pressurized infuser further comprises a pressure sensor, located within the container. This sensor is capable of measuring container pressure and is further capable of emitting a process signal indicative of measured container pressure, $P_m$. The process signal may be an analog or a digital signal.

The invention further comprises a flow control valve comprising a valve inlet and a valve outlet. The valve inlet is in fluid communication with the infusion fluid outlet port.

The invention further comprises a valve controller coupled to the flow control valve in order to control the position of the flow control valve in response to a control signal. The controller comprises a control signal receiver. The signal receiver may receive electrical signals or signals comprising electromagnetic energy, such as microwaves or radio waves.

The invention further comprises a programmable computer coupled to receive at least one signal from a pressure sensor indicative of container pressure. The computer comprises a memory comprising stored values for $V_i$, $P_i$, infusion time (K6), and a target infusion rate, TIR.

The computer further comprises algorithms derived from ideal gas laws, including $P_1V_1=P_2V_2$. The computer is capable of generating a control instruction based upon the pressure sensor signal and values stored in memory. The computer is further capable of sending a control signal, based upon the control instruction, to the control signal receiver. The computer can also calculate actual volume of fluid delivered and actual rate of delivery from measuring changes in $P_i$ and elapsed time.

The term "computer", as used herein, refers to a device comprising a central processing unit (CPU) or microprocessor, a memory capable of storing data, a clock, and a means of entering data into said memory. The term "computer", as used herein, is not intended to be limited to any specific type of computer architecture or platform. Those of ordinary skill in the computer arts will appreciate that there are a variety of hardware and software combinations that may be used to practice the present invention as it relates to the use of a programmable computer.

The term "algorithm", as used herein, refers to a set of instructions executable by a computer. Those of ordinary skill in the computer arts will appreciate that algorithms, as used in the present invention, may be written in many different programming languages and/or embedded into chips contained within a computer. The selection of computer language depends upon many factors, including but not limited to, computer hardware, programmer preference, and algorithm complexity. Such algorithms may be contained within an expert system of the types used in the artificial intelligence arts. The term "algorithm", as used herein, is not intended to be limited to any specific programming language, structure, or storage means.

A method embodiment of the present invention is directed toward the use of the above described autoinfuser in order to control the injection of infusion fluids into a patient. The method comprises measuring the initial pressure, $P_i$, of a pressurized controlled autoinfuser, inputting a target physiological parameter into a computer that controls the autoinfuser, attaching a physiological sensor capable of measuring a physiological parameter to a patient, inserting a vascular access device coupled to the flow control valve into the same patient, comparing measured data from the physiological sensor to a target physiological parameter to determine the difference, and using the measured difference to generate a control signal to the flow control valve of the autoinfuser. The method further comprises the use of ideal gas laws and algorithms, to control the infusion rate of infusion fluids into a patient.

Another embodiment of the present invention provides a method for delivering a preselected volume of infusion fluid into a patient within a preselected time. For example, a desired infusion time for 250 ml of hypertonic saline dextran (HSD) comprising 7.5% NaCl and 6% dextran 60, is 2–5 minutes. The infusion of this volume of HSD in less than two minutes may lead to complications, while infusion times longer than five minutes may be too slow to correct life threatening shock. Transient hypenatremia at dangerous levels occurs if HSD is infused too rapidly. It has also been observed that rapid infusion of HSD may result in acute transient hypotension as manifested by subnormal arterial blood pressure, as discussed in Kien et al., "Acute Hypotension Caused By Rapid Hypertonic Saline Infusion In Anesthetized Dogs", Anesthesia and Analgesia 73: 597–602, 1991.

DESCRIPTION OF THE PREFERRED EMBODIMENTS

An apparatus embodiment of the invention comprises a pressurized infuser 22 comprising a fluid volume pressure container 24 having a known initial volume of pressurized fluid occupying a known initial volume, $V_i$, and a known initial pressure, $P_i$. In a preferred embodiment, the pressure container is rigid and the fluid it contains is a gas.

Figure 1:
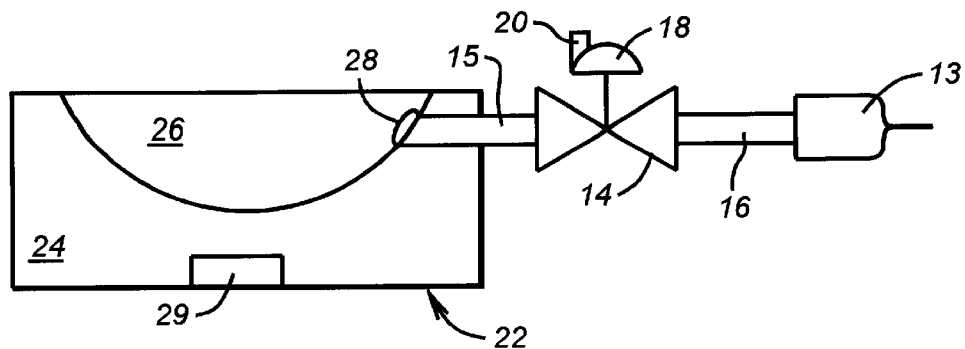
FIG. 1 is a side view of an apparatus embodiment of the present invention.

A flexible infusion bag 26 having volume $V_f$, is contained within the pressure container. An infusion fluid outlet port 28 is in fluid communication with the bag as shown in FIG. 1. A pressure sensor 29 is located within the container. The pressure sensor is capable of measuring container pressure and emitting a process signal indicative of measured container pressure, $P_m$, as shown in FIG. 1.

Figure 2:
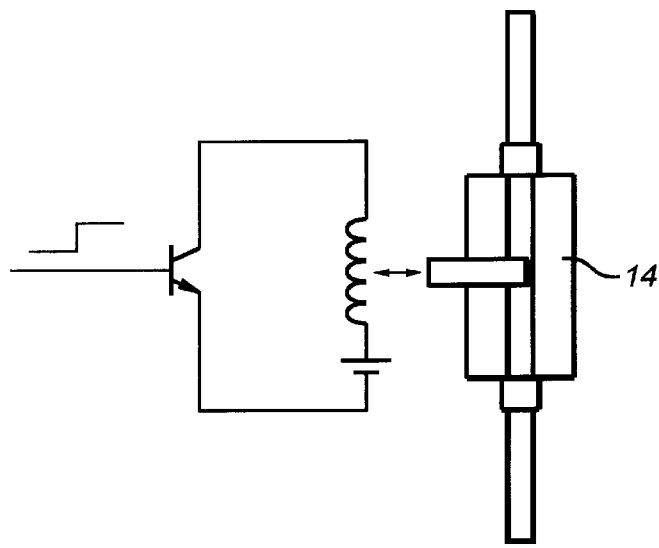
FIG. 2 is a schematic diagram of a solenoid valve of the present invention.

The invention further comprises a flow control valve 14 comprising a valve inlet 15 and a valve outlet 16. The inlet is in fluid communication with the outlet port of the container, as shown in FIG. 1. In a preferred embodiment, the flow control valve is a solenoid valve, as shown in FIG. 2. Other electromechanical devices may be used for the flow control valve. In a preferred embodiment, a pressure regulator is installed between the outlet port and the flow control valve.

This embodiment of the invention further comprises a valve controller 18 coupled to the valve to control the position of the valve in response to a control signal. The controller comprises a control signal receiver 20, as shown in FIG. 1. Those persons of ordinary skill in the instrumentation arts will appreciate that a variety of signal receivers are suitable for this application, including but not limited to, electrical or electromagnetic signal receivers.

Figure 3:
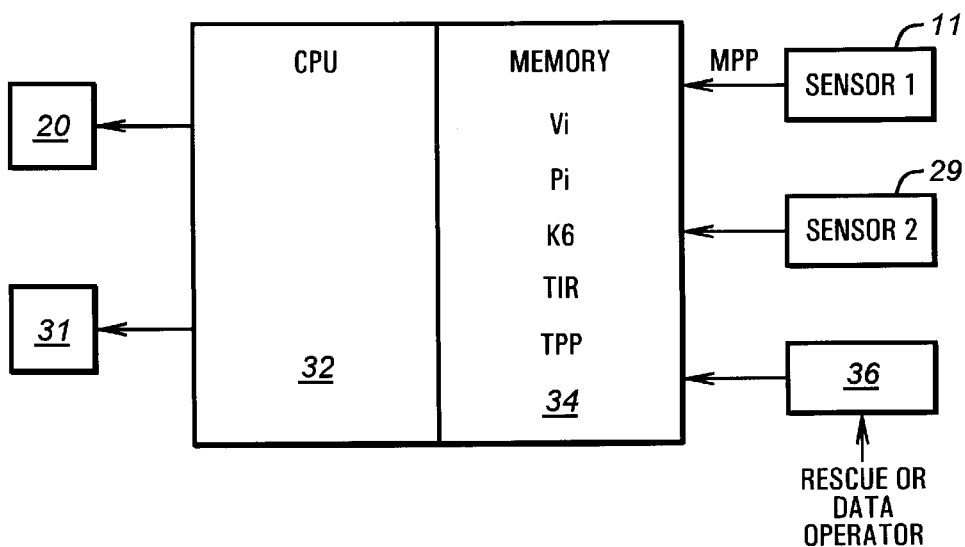
FIG. 3 is a block diagram of an apparatus embodiment of the present invention.

One embodiment of the invention comprises a physiological sensor 11 attachable to a patient. The physiological sensor is capable of measuring a physiological parameter, such as blood pressure, blood or tissue oxygenation, blood or tissue lactate, cardiac output, tissue blood flow, or acid base status. The physiological sensor is further capable of transmitting a signal indicative of a measured physiological parameter, MPP as shown in FIG. 3. In other embodiments, the invention may comprise more than one physiological sensor. In another embodiment, the invention does not comprise a physiological sensor. The time dependency of the MPP is represented by the notation "MPP(t)."

This embodiment of the invention further comprises a programmable computer 32 coupled to receive input signals from the pressure sensor and the physiological sensor, indicative of container pressure and the measured physiological parameter, respectively. The computer comprises a memory 34 comprising stored values for $V_i$, $P_i$, infusion time period K6, and a target physiological parameter value TPP, as shown in FIG. 3. In one embodiment of the invention, the computer comprises a clock capable of measuring the time that the flow control valve is open or closed. In another embodiment, the clock is external to the computer and is configured to send a timing signal to the computer indicative of the time that the flow control valve is open or closed.

Figure 6A:
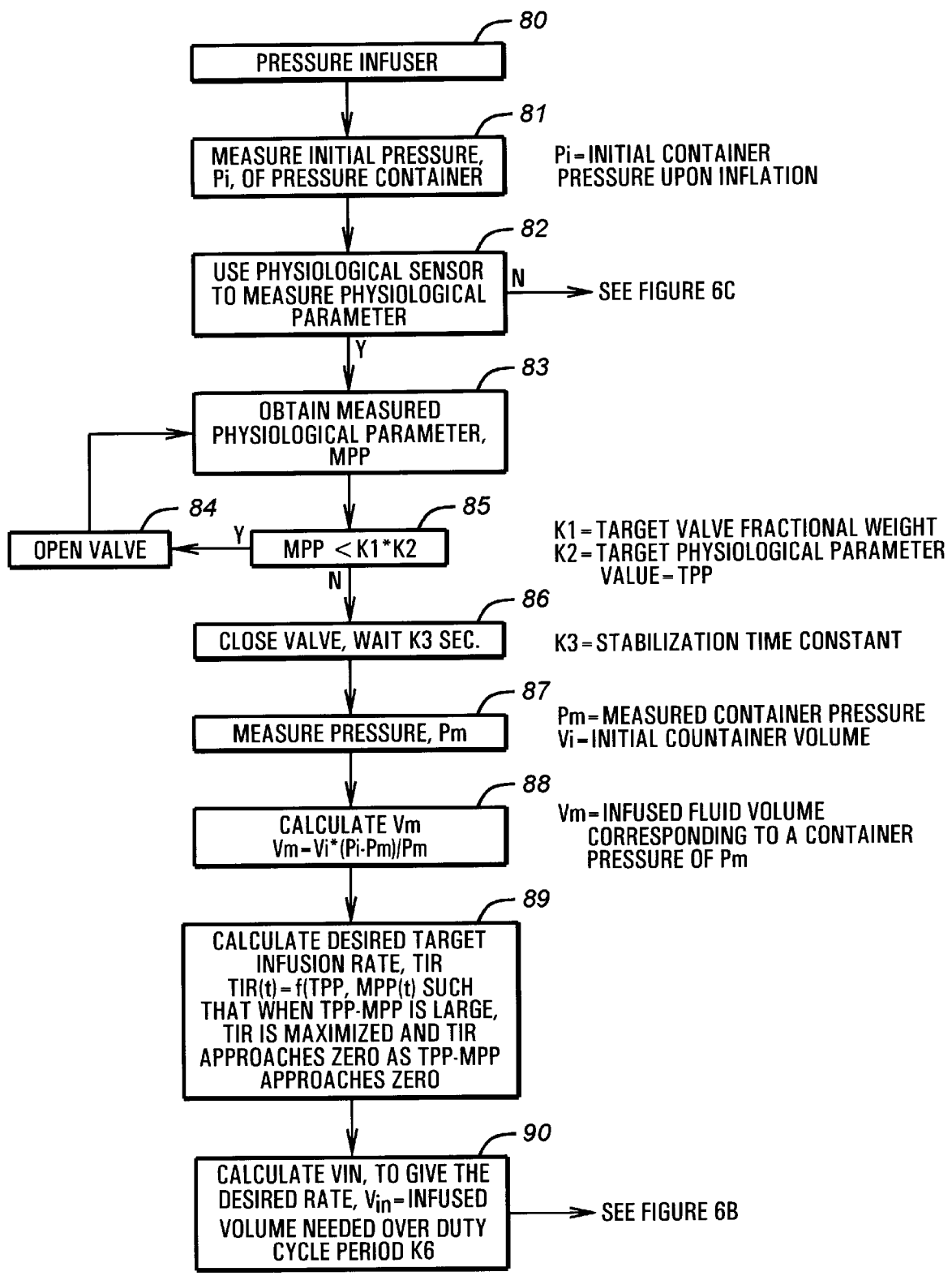
FIGS. 6A–6C are block diagrams of alternative methods of practicing the present invention, with and without the use of a physiological sensor.
Figure 6B:
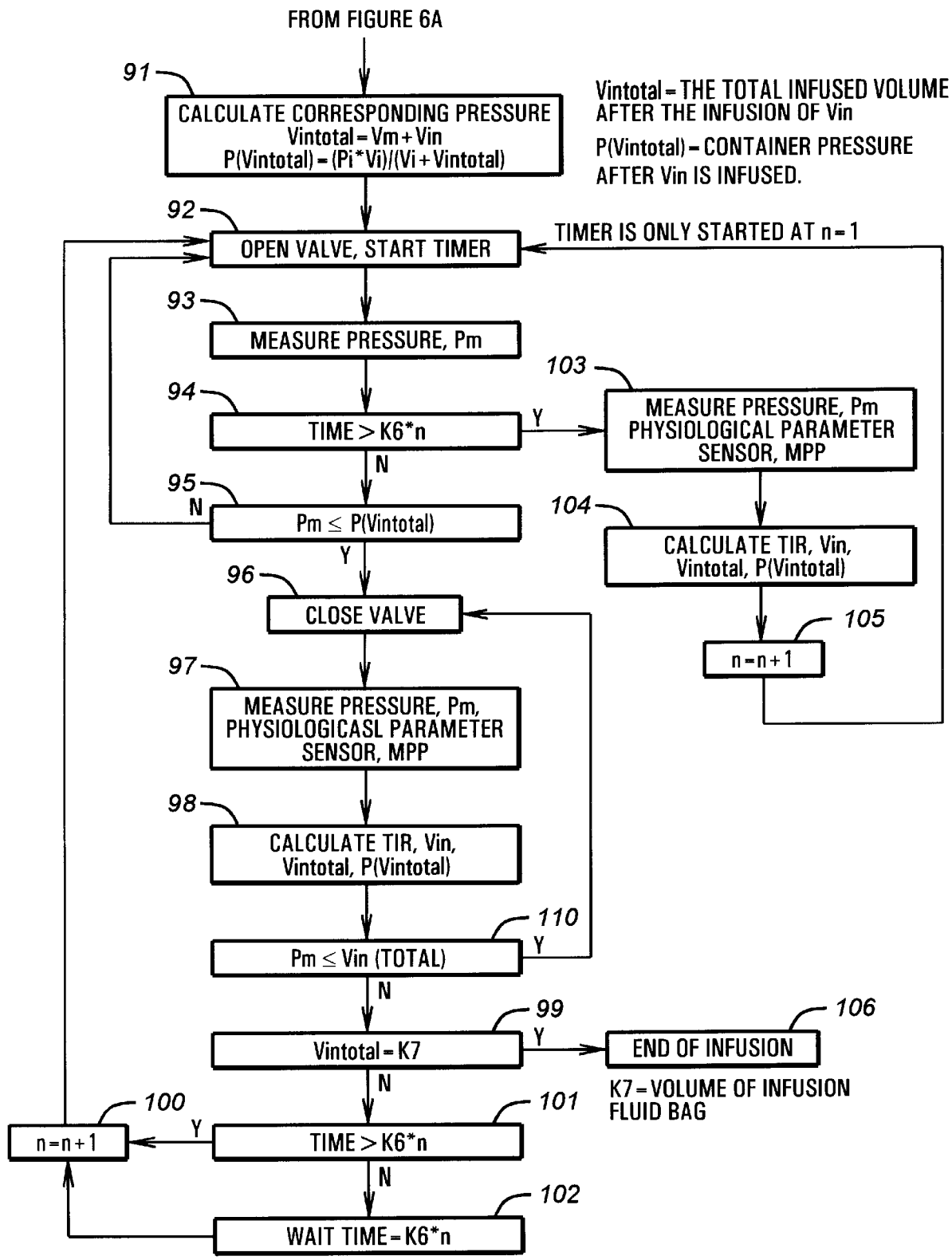
Figure 6C:
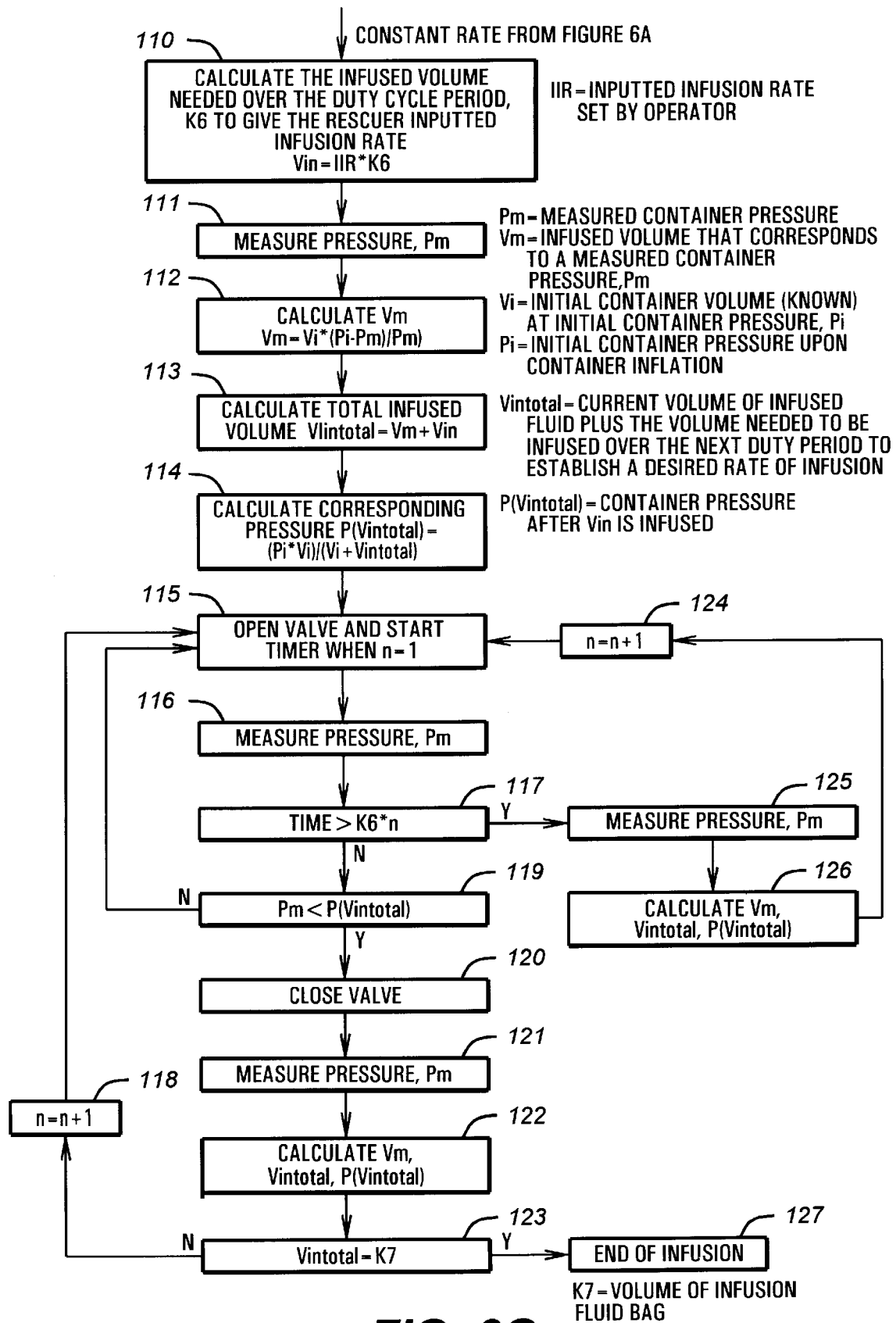

The computer further comprises algorithms capable of comparing the target physiological parameter TPP to the measured physiological parameter MPP and further capable of generating at least one control instruction based upon this parameter comparison and further based upon the pressure sensor signal and values stored in memos as shown in FIGS. 6A and 6B. The computer is capable of sending a control signal, based upon the control instructions, to the control signal receiver. A variety of algorithms that may be used in practicing the invention are shown in FIGS. 6A–6C.

In the embodiment where no physiological sensor is used, the computer memory comprises stored values for $V_i$, $P_i$, K6, and target infusion rate (TIR). The computer further comprises algorithms derived from the combined gas laws. Such algorithms are used in this embodiment of the invention to generate a control instruction based upon the pressure sensor signal and values stored in memory as shown in FIG. 6A and 6C.

In other preferred embodiments, the invention further comprises a data input terminal 36 capable of receiving data from an external source and transmitting input data to the memory. The data input terminal may be employed with and without a physiological sensor. In a preferred embodiment, the invention further comprises a data output terminal or display 31.

Figure 5A:
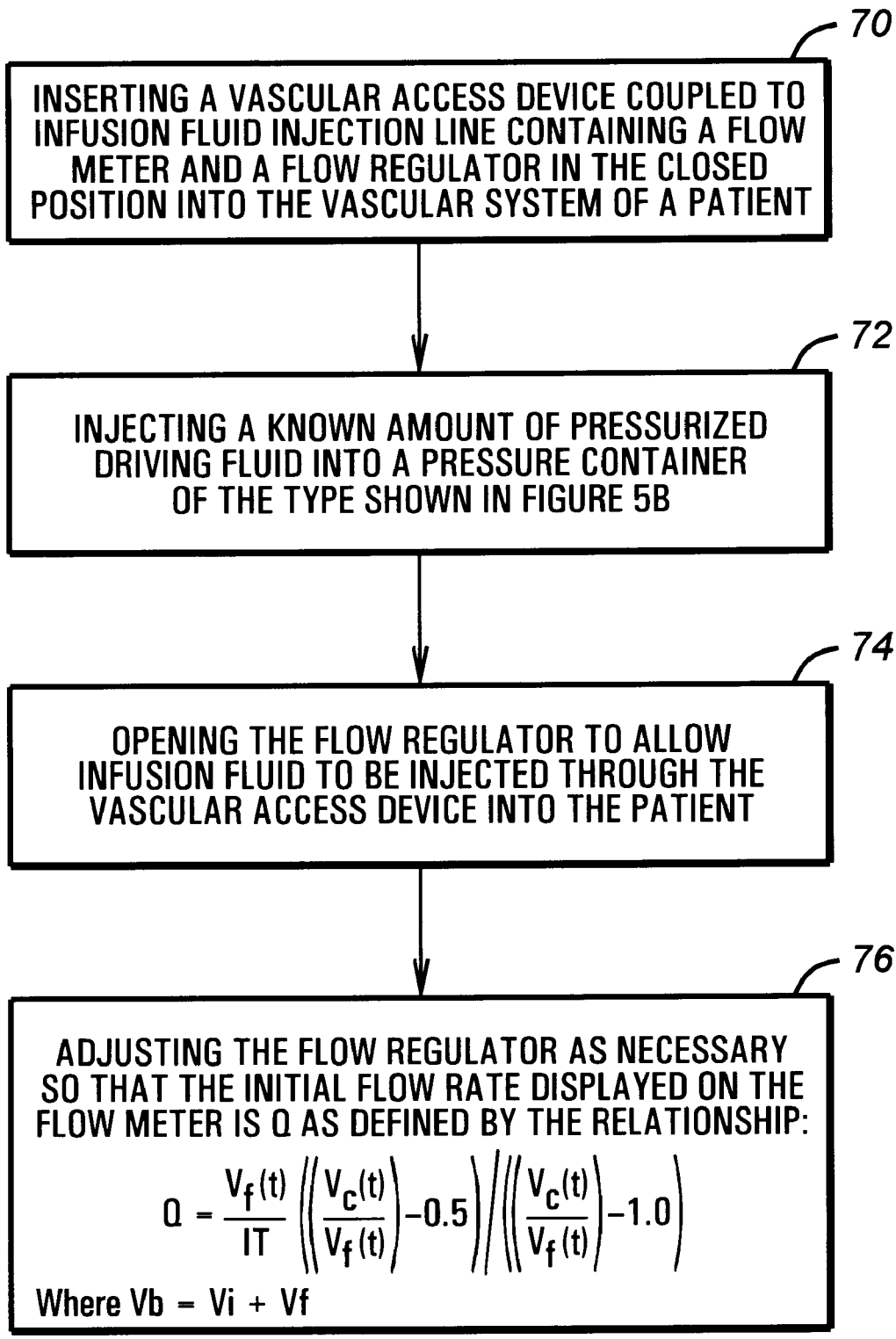
FIGS. 5A and 5C are block diagrams of two other method embodiments of the present Invention.
Figure 5B:
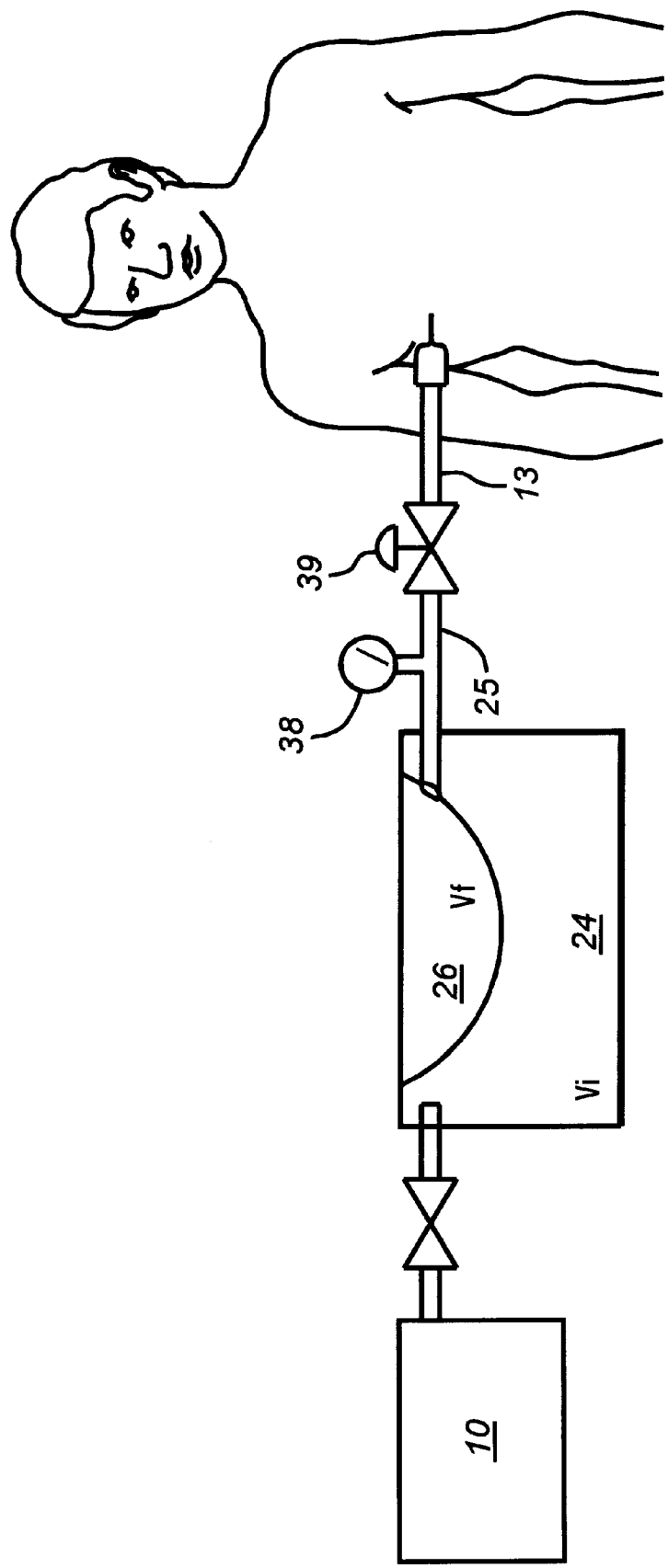
FIG. 5B is a side view of another apparatus embodiment of the invention.

In a preferred embodiment, the invention further comprises a vascular access device 13 coupled to the valve outlet port. In one embodiment of the present invention, the vascular access device is an intravenous device. In another embodiment of the present invention, the vascular access device is an intraosseous device 13, as shown in FIG. 5B.

The invention is also directed to a method of controlling the injection of infusion fluids into a patient without the use of a pump. The first step of this method embodiment of the invention is directed to measuring the initial pressure, $P_i$, of a pressurized computer controlled autoinfuser comprising a pressure container having a known initial volume $V_i$, of pressurized fluid and a flow control valve comprising a valve inlet and a valve outlet, as shown in block 50 of FIG. 4. In a preferred embodiment, the pressurized fluid is a gas.

Figure 4:
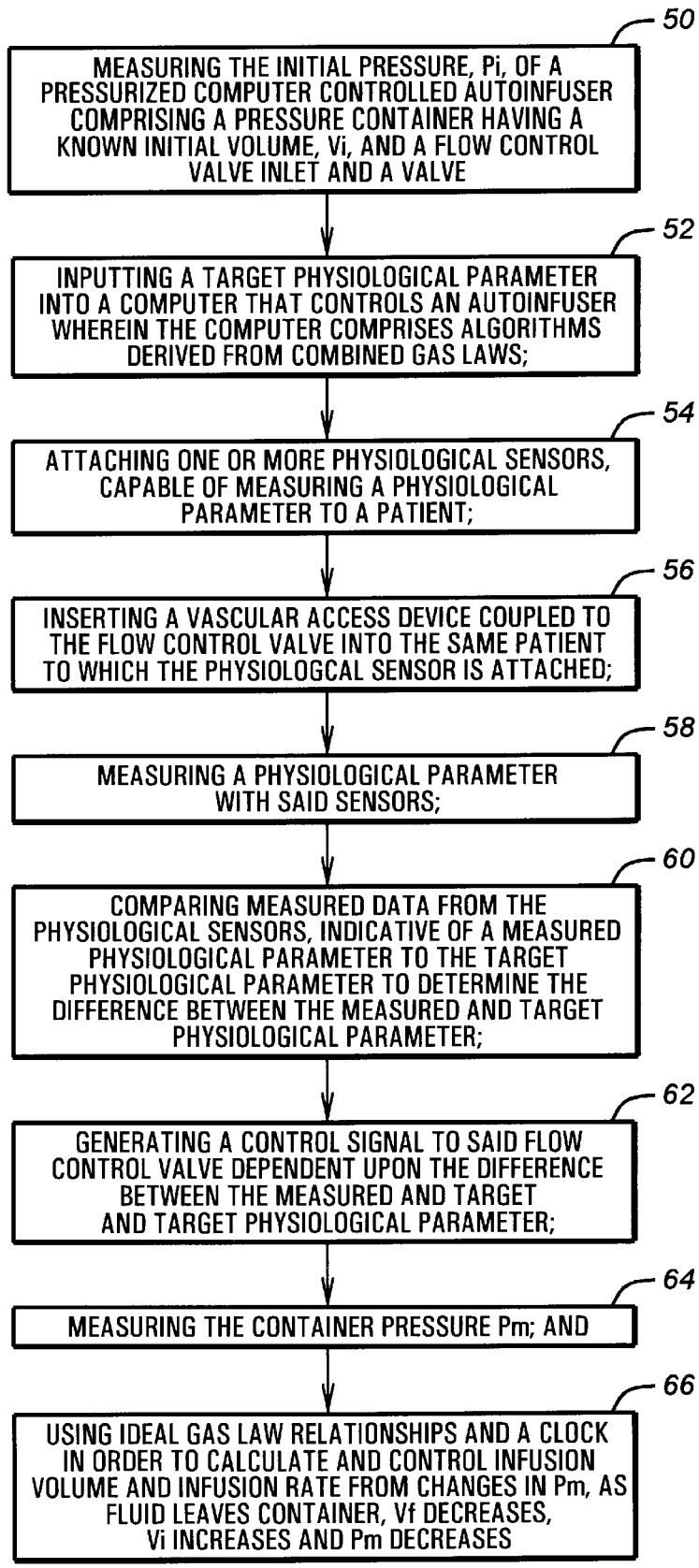
FIG. 4 is a block diagram of one method embodiment of the present invention.

The second step of this method is inputting a target physiological parameter into a computer that controls an autoinfuser wherein the computer comprises an expert system comprising algorithms derived from combined gas laws, as shown in block 52 of FIG. 4.

The third step of this method is attaching a physiological sensor capable of measuring a physiological parameter to a patient, as shown in block 54 of FIG. 4. The fourth step of this method is inserting a vascular access device coupled to the flow control valve into the same patient to which the physiological sensor is attached, as shown in block 56 of FIG. 4.

The fifth step of this method is measuring a physiological parameter of the patient as depicted in block 58 of FIG. 4. In a preferred embodiment, the measured physiological parameter is blood pressure.

The sixth step of this method is comparing measured data from the physiological sensor, indicative of a measured physiological parameter, to the target physiological parameter, in order to determine the difference between the measured and target physiological parameters, as shown in block 60 of FIG. 4.

The seventh step of this method is generating a control signal to the flow control valve, dependent upon the difference between the measured and target physiological parameters, as shown in block 62 of FIG. 4.

The eighth step of this method is measuring the container pressure $P_m$, as shown in block 64 of FIG. 4. $P_m$ represents the container pressure after infusion fluid volume $V_m$ has been injected from the infusion bag into the patient.

The last step of this method is using ideal gas law relationships between $P_i$, $P_m$, $V_m$ and $V_i$ and a clock, to calculate the volume infused and the infusion rate in order to control the rate and volume of fluid delivered from the autoinfuser to a patient, as shown in block 64 of FIG. 4. These relationships include:

$$P_i V_i = P_2 V_2 \tag{1}$$

In equation (1), when $P_2=P_m$, $V_2$ is the volume of pressurized gas in the pressure container after infusion fluid volume $V_m$ has been injected from the infusion fluid bag into a patient, as defined by equation (2);

$$V_2 = V_i + V_m \tag{2}$$

Thus, where $P_2=P_m$, equations (3a) and (3b) define an application of the ideal gas laws to the present invention;

$$P_i V_i = P_m (V_i + V_m) \tag{3a}$$

$$V_m = (V_i / P_m)(P_i - P_m) \tag{3b}$$

Equation (3b) is derived algebraically from equation (3a). Equation (3b) appears in block 88 of FIG. 6a.

Another method of embodiment of the present invention does not require a microprocessor. This method is directed toward injecting infusion fluids into a patient during an injection time interval IT, as shown in FIG. 5A. An apparatus that may be used in practicing this method is depicted in FIG. 5B. As shown in FIG. 5B, the apparatus comprises a container of pressurized driving fluid 10 having an injection outlet 95. The apparatus further comprises a driving fluid valve 96 having an inlet 97 coupled to the injection outlet and a discharge section 98 in fluid communication with the pressure container 24.

Another first step of this method is inserting a vascular access device coupled to an infusion fluid injection line containing a flow meter 38 and a flow regulator 39 into the vascular system of a patient, as shown in block 70 of FIG. 5A and in FIG. 5B. During this step, the flow regulator is in the closed position.

The second step of this method is injecting a known amount of pressurized driving fluid into a pressure container having a known initial volume, $V_i(t_o)$, a time dependent volume $V_i(t)$, and comprising a flexible infusion bag having a known initial volume of infusion fluid, $V_f(t_o)$ and a time dependent volume $V_f(t)$. The infusion bag is in fluid communication with the vascular access device, as shown in block 72 of FIG. 5A.

The third step of this method is opening the flow regulator to allow infusion fluid to leave the container and infusion bag and to be injected through the vascular access device into the patient, as shown in block 74 of FIG. 5A.

The last step of this method is adjusting or setting the flow regulator as necessary so that the initial flow rate displayed on the flow meter is Q, wherein Q is defined by the relationship:

(4)

$$Q = \frac{V_f(t)}{IT}\left(\left(\frac{V_c(t)}{V_f(t)}\right) - 0.5\right) / \left(\left(\frac{V_c(t)}{V_f(t)}\right) - 1.0\right) \tag{4}$$

where $V_c(t)=V_i(t)+V_f(t)$ This step is depicted in block 76 of FIG. 5A.

In this embodiment of the invention, the volume of the pressurized driving fluid is substantially less than $V_f$ and the pressurized driving fluid expands as it fills the pressure container, such that pressure at time $t_1$, denoted by P(t), is expressed by the ideal gas law as:

$$P(t)(V_c(t)-V_i(t))=P(t)(V_c(t)-V(t))=C_1 \quad (5)$$

where C is a constant P(t) is the pressure of the pressure container at time t, and $V_f(t)$ is the volume of the infusion fluid bag at time, t.

The flow of fluid into a patient, Q. is proportional to the pressure of the driving fluid, such that:

$$Q=-dv/dt=K^*P(t) \quad (6)$$

where K is a constant of proportionality. Equations (5) and (6) can be rearranged algebraically to give equation (7):

$$dt=(-1/C^*K)(V_c(t)-V(t))dv \quad (7)$$

Equation (7) is integrated as follows:
(8)

$$\int_o^t dt = -\frac{1}{C*K}\int_{V_i}^{V}(V_c(t)-V(t))dv \quad (8)$$

The integration shown in equation (8) yields the following relationship:
(9)

$$t=-\frac{-1}{(C*K)}\left(V_c(t)V(t)-\frac{V^2(t)}{2}-V_c(t)V_f(t)+\frac{V_f^2(t)}{2}\right) \quad (9)$$

When the infusion fluid injection is completed at time t=IT and V(t)=0, equation 9 yields:
(10)

$$IT = \frac{\left(V_c(t)V_f(t)-\frac{V_f^2(t)}{2}\right)}{(C*K)} \quad (10)$$

Equations (5), (6), and (10) can be combined to yield equation (11) as follows:
(11)

$$IT = \frac{\left(V_c(t)V_f(t)-\frac{V_f^2(t)}{2}\right)}{\left(P_1(V_c(t)-V_f(t))\left(\frac{QI}{P_1}\right)\right)} \quad (11)$$

Equation (4) is derived from an algebraic manipulation of equation (11).

In a preferred embodiment of this method, the vascular access device is an intraosseous device 13 as shown in FIG. 5B. In another embodiment of this method of the invention, the injection time IT is greater than two minutes and less than five minutes. In another embodiment of this method of the invention, the infusion fluid comprises hypertonic saline dextran. In another embodiment of this method of the invention, the volume of infusion fluid, $V_i$, is in the range of 200–300 ml. and the infusion fluid is a small volume hypertonic solution. In another embodiment the fluid is an isotonic crystalloid such as lactated Ringers and $V_f$ is in the range of 800–1200 ml. In another embodiment, the infusion fluid is an isotonic colloid or a blood substitute and $V_f$ is in the range of 400–600 ml.

Figure 5C:
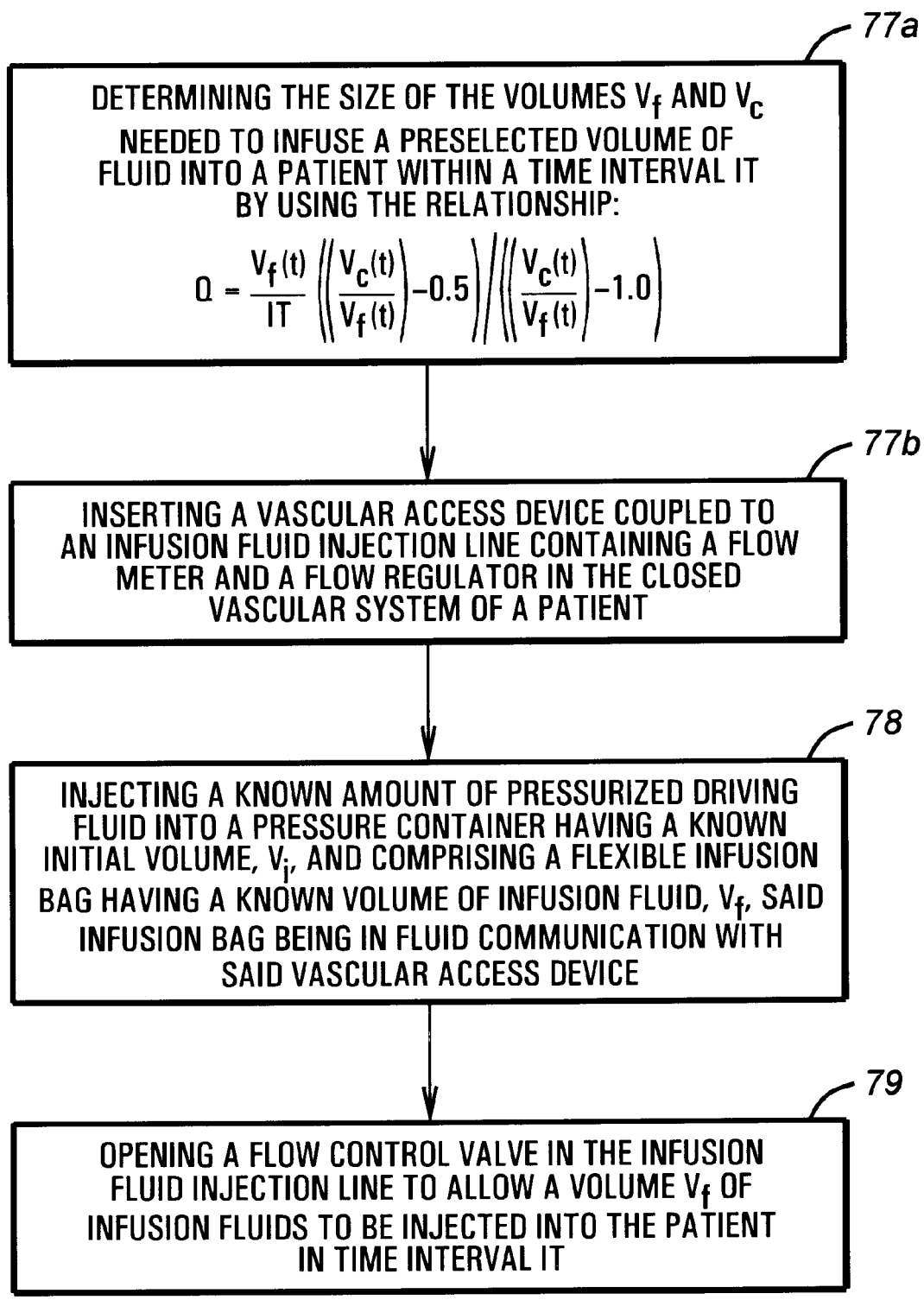

In another embodiment of the invention, as shown in FIG. 5C, there is no flow meter and the flow regulator is not adjusted. Rather initial pressures, volumes and output resistances are chosen in order that the $V_f$ fluid will be delivered within a target time interval, IT, using the relationship shown in equation (4), based on usual resistances associated with vascular access devices and usual patient parameters, as shown in block 77a of FIG. 5C. A vascular access device coupled to an infusion fluid injection line containing a flow control valve is inserted into the vascular access system of a patient, as shown in block 77b of FIG. 5C. A known amount of pressurized driving fluid is injected into a container, as shown in block 78 of FIG. 5C. The flow control valve in the infusion fluid injection line is then opened to allow a volume, $V_f$, of infusion fluids to be injected into the patient in time interval IT, as shown in block 79 of FIG. 5C.

The foregoing disclosure and description of the invention are illustrative and explanatory. Various changes in the size, shape, and materials, as well as in the details of the illustrative construction may be made without departing from the spirit of the invention.

What is claimed is:

1. An apparatus for injecting infusion fluids into a patient at a controlled infusion rate, comprising:
   a. a pressurized infuser comprising a pressure container having a known initial volume, $V_i$, and a known initial pressure, $P_i$, a flexible infusion fluid bag having volume $V_f$, contained within said pressure container, an infusion fluid outlet port in fluid communication with said bag, a pressure sensor located within said container and capable of measuring container pressure and emitting a process signal indicative of measured container pressure, $P_m$;
   b. a flow control valve comprising a valve inlet and a valve outlet, said inlet being in fluid communication with said infusion fluid outlet port;
   c. a valve controller coupled to said valve to control the position of said valve in response to a control signal, said controller comprising a control signal receiver, and
   d. a programmable computer coupled to receive at least one signal from said pressure sensor indicative of container pressure, said computer having a memory comprising stored values for $V_i$, $P_i$, infusion time period, K6, a target infusion rate, TIR, and said computer further comprising algorithms derived from ideal gas laws, said computer being capable of generating a control signal based upon said pressure sensor signal and said stored values, said computer further being capable of sending a control signal based upon said control instruction to said control signal receiver.

2. The apparatus of claim 1, wherein said flow control valve is a solenoid valve.

3. The apparatus of claim 1, wherein said pressure container comprises a gaseous driving fluid.

4. The apparatus of claim 1, further comprising a data input terminal electrically coupled to said memory capable of receiving data from an external source and transmitting inputted data to said memory.

5. The apparatus of claim 1, further comprising a vascular access device in fluid communication with said valve outlet.

6. The apparatus of claim 5, wherein said access device is an intraosseous device.

7. The apparatus of claim 1, wherein said pressure container is rigid.

8. The apparatus of claim 1 further comprising:
   a. a container of pressurized driving fluid having an injection outlet;

b. a driving fluid valve having an inlet coupled to said injection outlet and a discharge section in fluid communication with said pressure container.

9. An apparatus for injecting infusion fluids into a patient at a controlled infusion rate, comprising:

a. a pressurized infuser comprising a pressure container having a known initial volume, $V_i$, and a known initial pressure, $P_i$, a flexible infusion fluid bag having volume $V_f$, contained within said pressure container, an infusion fluid outlet port in fluid communication with said bag, a pressure sensor located within said container and capable of measuring container pressure and emitting a process signal indicative of measured container pressure, $P_m$;

b. a flow control valve comprising a valve inlet and a valve outlet, said inlet being in fluid communication with said outlet infusion fluid port;

c. a valve controller coupled to said valve to control the position of said valve in response to a control signal, said controller comprising a control signal receiver;

d. a physiological sensor attachable to a patient and capable of measuring a physiological parameter, and transmitting a signal indicative of said measured physiological parameter MPP; and e. a programmable computer electrically coupled to receive input signals from said pressure sensor and said physiological sensor, indicative of container pressure and said measured physiological parameter, respectively, said computer further comprising a memory comprising stored values for $V_i$, $P_i$, infusion time period K6, and a target physiological parameter value, TPP, and further comprising algorithms derived from combined gas laws, said algorithms being capable of comparing said target physiological parameter to said measured physiological parameter and further capable of generating at least one control instruction based upon said parameter comparison and further based upon said pressure sensor signal and values stored in memory, said computer further being capable of sending a control signal, based upon said control instruction, to said control signal receiver.

10. The apparatus of claim 9, wherein said measured physiological parameter is blood pressure.

11. The apparatus of claim 9 where said measured physiological parameter is indicative of blood or tissue oxygenation or of blood or tissue lactate.

12. The apparatus of claim 9, further comprising a vascular access device coupled to said valve outlet.

13. The apparatus of claim 9 wherein said pressure container is rigid.

* * * * *